US005463023A

United States Patent [19]

Schreiber et al.

[11] Patent Number: 5,463,023

[45] Date of Patent: Oct. 31, 1995

[54] COMPOSITION FOR INHIBITION OF INTRACELLULAR TRANSCRIPTION

[75] Inventors: Robert D. Schreiber; Andrew C. Greenlund, both of St. Louis, Mo.; Michael A. Farrar, Seattle, Wash.

[73] Assignee: Washington University, St. Louis, Mo.

[21] Appl. No.: 141,499

[22] Filed: Oct. 22, 1993

[51] Int. Cl.$^6$ ................................ C07K 7/00; C07K 7/04

[52] U.S. Cl. ........................... 530/327; 530/328; 530/330

[58] Field of Search ............................ 435/7.1; 530/330, 530/327, 328; 514/2, 7, 15, 17

OTHER PUBLICATIONS

Aguet et al. "Molecular Cloning and Expression of the Human Interferon–α Receptor", Cell, vol. 55, Oct. 21, 1988, pp. 273–280.

Farrar et al. "Identification of a Functionally Important Sequence in the C Terminus of the Interferon–α Receptor", PNAS, vol. 89, Dec. 1992, pp. 11706–11710.

Pearse et al. "Interferon α–Induced Transcription of the High–Affinity Fc Receptor for Ig G Requires Assembly of a Complex That Includes the 91–KDa Subunit of Transcription Factor ISGF3", PNAS, vol. 90, May 1993, pp. 4314–4318.

Michael A. Farrar, Jose Fernandez–Luna, and Robert D. Schreiber, *Identification of Two Regions within the Cytoplasmic Domain of the Human Interferon–y Receptor Required for Function,* "The Journal of Biological Chemistry", vol. 266, No. 29, Issue of Oct. 15, pp. 19626–19635, 1991.

Chris Schindler, Xin–Yuan Fu, Teresa Improta, Ruedi Aebersold, and James E. Darnell, Jr., *Proteins of transcription factor ISGF–3: One gene encodes the 91–and 84–kDa ISGF–3 proteins that are activated by interferon α, "Proc. Natl. Acad. Sci. USA", vol. 89, pp. 7836–7839, Aug. 1992.*

Xin–Yuan Fu, *A Transcription Factor with SH2 and SH3 Domains Is Directly Activated by an Interferon α–Induced Cytoplasmic Protein Tyrosine Kinase(s), "Cell", vol. 70, 323–335, Jul. 24, 1992.*

Kevin C. Wilson and David S. Finbloom, Interferon y rapidly induces in human monocytes a DNA–binding factor that recognizes the y response region within the promoter of the gene for the high–affinity Fcy receptor, "Proc. Natl. Acad. Sci. USA", vol. 89, pp. 11964–11968, Dec. 1992.

Andrew C. Greenlund, Robert D. Schreiber, David V. Goeddel, and Diane Pennica, *Interferon–y Induces Receptor Dimerization in Solution and on Cells,* "The Journal of Biological Chemistry", vol. 268, No. 24, Issue of Aug. 25, pp. 18103–18110, 1993.

Kenichi Igarashi, Michael David, David S. Finbloom, and Andrew C. Larner, *In Vitro Activation of the Transcription Factor Gamma Interferon Activation Factor by Gamma Interferon: Evidence for a Tyrosine Phosphatase/Kinase Signaling Cascade,* "Molecular and Cellular Biology", Mar. 1993, pp. 1634–1640, vol. 13, No. 3.

Chris Schindler, Ke Shuai, Vincent R. Prezioso, James E. Darnell, Jr., *Inteferon–Dependent Tyrosine Phosphorylation of a Latent Cytoplasmic Transcription Factor,* "Science", vol. 257, pp. 809–813, Aug. 7, 1992.

Ken–Ichi Igarashi, Michael David, Andrew C. Larner, and David S. Finbloom, *In Vitro Activation of a Transcription Factor by Gamma Interferon Requires a Membrane–Associated Tyrosine Kinase and Is Mimicked by Vanadate,* "Molecular and Cellular Biology", Jul. 1993, pp. 3984–3989, vol. 13, No. 7.

Michael A Farr, Jacqueline D. Campbell, and Robert D. Schreiber, *Identification of a functionally important sequence in the C terminus of the interferon–y receptor,* "Proc. Natl. Acad. Sci. USA", vol. 89, pp. 11706–11710, Dec. 1992.

Xin–Yuan Fu, Chris Schindler, Teresa Improta, Ruedi Aebersold, and James E. Darnell, Jr., *The proteins of ISGF–3, the interferon α–induced transcriptional activator, define a gene family involved in signal transduction,* "Proc. Natl. Acad. Sci. USA", vol. 89, pp. 7840–7843, Aug. 1992.

Sudip K. Bandyopadhyay and Ganes C. Sen, *Role of Protein Phosphorylation in Activation of Interferon–stimulated Gene Factors,* "The Journal of Biological Chemistry", vol. 267, No. 9, Issue of Mar. 25, pp. 6389–6395, 1992.

Michael David, Guillermo Romero, Zhong–Yin Zhang, Jack E. Dixon, and Andrew C. Larner, *In Vitro Activation of the Transcription Factor ISGF3 by Interferon α Involves a Membrane–associated Tyrosine Phosphatase and Tyrosine Kinase,* "The Journal of Biological Chemistry", vol. 268, No. 9, Issue of Mar. 25, pp. 6593–6599, 1993.

Ke Shuai, Chris Schindler, Vincent R. Prezioso, James E. Darnell, Jr., *Activation of Transcription by IFN–y: Tyrosine Phosphorylation of a 91–kD DNA Binding Protein,* "Science", vol. 258, pp. 1808–1812, Dec. 11, 1992.

*Primary Examiner*—Mindy B. Fleisher
*Assistant Examiner*—David Guzo
*Attorney, Agent, or Firm*—Rogers, Howell & Haferkamp

[57] ABSTRACT

Novel compositions and methods that result in the inactivation of IFNγ inducible transcription factors by binding to the transcription factor in the cell and inhibiting the transcriptional activity of the factors are disclosed. The composition comprises an isolated peptide that contains the amino acid sequence $Xaa_1$-Asp-$Xaa_2$-$Xaa_3$-His where $Xaa_1$ is phosphorylated tyrosine and $Xaa_2$ and $Xaa_3$ are any amino acid, or derivatives and functional equivalents thereof, that is capable of specifically binding to the p91 family of IFNγ inducible transcription factors in a cell. A method for inhibiting the intracellular activation of a transcription factor by introducing into a cell an effective amount of a peptide that contains the 5 amino acid sequence described or a derivative thereof, which specifically binds to a transcription factor in the cell is also provided.

2 Claims, 11 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Modified-site
( B ) LOCATION: 1
( D ) OTHER INFORMATION: /note="Xaa IS PHOSPHORYLATED TYROSINE"

( x i ) SEQUENCE DESCRIPTION: SEQ ID NO:1:

```
Xaa Asp Xaa Xaa His
1               5
```

( 2 ) INFORMATION FOR SEQ ID NO:2:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

```
Tyr Asp Lys Pro His
1               5
```

-continued ( 2 ) INFORMATION FOR SEQ ID NO:3:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Modified-site
( B ) LOCATION: 5
( D ) OTHER INFORMATION: /note="Xaa IS PHOSPHORYLATED TYROSINE"

( x i ) SEQUENCE DESCRIPTION: SEQ ID NO:3:

Thr Ser Phe Gly Xaa Asp Lys Pro His
1 5

( 2 ) INFORMATION FOR SEQ ID NO:4:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Modified-site
( B ) LOCATION: 5
( D ) OTHER INFORMATION: /note="Xaa IS PHOSPHORYLATED TYROSINE"

( x i ) SEQUENCE DESCRIPTION: SEQ ID NO:4:

Thr Ser Phe Gly Xaa Asp Lys Pro His Val Leu Val
1 5 10

( 2 ) INFORMATION FOR SEQ ID NO:5:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

CCTCCTTTGG TTTTGATAAA C 21

( 2 ) INFORMATION FOR SEQ ID NO:6:

( i ) SEQUENCE CHARACTERISTICS:
( A ) LENGTH: 21 base pairs

-continued ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GTTTATCAAA ACCAAAGGAG G 21

( 2 ) INFORMATION FOR SEQ ID NO:7:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TGTATCACTC ATCACGTCAT TCCAGCCATT TTCGTTAGAA AAGG 44

( 2 ) INFORMATION FOR SEQ ID NO:8:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

ATGACGTGAT GAGTGATACA AATTTTGATT CAGG 34

( 2 ) INFORMATION FOR SEQ ID NO:9:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

CGCTTTGAAC TCGTTTCAAT ACAG 24

( 2 ) INFORMATION FOR SEQ ID NO:10:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

CTGGAGTGAA ACGAGTTCAA AGCGATG 27

( 2 ) INFORMATION FOR SEQ ID NO:11:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CCATCGATGT CATGAAAATT CTTTGGAATC TTCTGTTGGT CTAAAACCAA TC 52

( 2 ) INFORMATION FOR SEQ ID NO:12:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

ATGTATTTCC CAGAAA 16

( 2 ) INFORMATION FOR SEQ ID NO:13:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

CTTTTCTGGG AAATA 15

( 2 ) INFORMATION FOR SEQ ID NO:14:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

-continued ( i i i ) HYPOTHETICAL: NO ( i v ) ANTI-SENSE: NO ( x i ) SEQUENCE DESCRIPTION: SEQ ID NO:14:

GATCCATGCC TCGGGAAAGG GAAACCGAAA CTGAAGCCAC 40

( 2 ) INFORMATION FOR SEQ ID NO:15:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

Thr Ser Phe Gly Tyr Asp Lys Pro His
1 5

( 2 ) INFORMATION FOR SEQ ID NO:16:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Modified-site
( B ) LOCATION: 5
( D ) OTHER INFORMATION: /note="Xaa IS PHOSPHORYLATED TYROSINE"

( x i ) SEQUENCE DESCRIPTION: SEQ ID NO:16:

Thr Ser Phe Gly Xaa Ala Lys Pro Ala
1 5

( 2 ) INFORMATION FOR SEQ ID NO:17:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
( A ) NAME/KEY: Modified-site
( B ) LOCATION: 5
( D ) OTHER INFORMATION: /note="Xaa IS PHOSPHORYLATED -continued

TYROSINE"

( x i ) SEQUENCE DESCRIPTION: SEQ ID NO:17:

Ser Leu Ile Gly Xaa Arg Pro Thr Glu Asp Ser Lys
1 5 10

( 2 ) INFORMATION FOR SEQ ID NO:18:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

Thr Ser Phe Gly Tyr Asp Lys Pro His Val Leu Val
1 5 10

( 2 ) INFORMATION FOR SEQ ID NO:19:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
( A ) NAME/KEY: Modified-site
( B ) LOCATION: 5
( D ) OTHER INFORMATION: /note="Xaa IS PHOSPHORYLATED TYROSINE"

( x i ) SEQUENCE DESCRIPTION: SEQ ID NO:19:

Thr Ser Phe Gly Xaa Ala Lys Pro Ala Val Leu Val
1 5 10

COMPOSITION FOR INHIBITION OF INTRACELLULAR TRANSCRIPTION

This invention was made with Government support under Grant No. CA 43059 awarded by the National Institutes of Health. The Government has certain rights in the invention.

BACKGROUND OF THE INVENTION (1) Field of the Invention

This invention relates in general to the activity of interferonγ (IFNγ), and more particularly to a composition capable of the intracellular inhibition of an interferonγ activatable transcription factor that is involved in the activation of interferonγ inducible genes, and a method for inhibiting such a transcription factor.

(2) Description of Background Art

Interferon-γ (IFNγ) is an important cytokine derived from T cells and natural killer cells that plays important roles in promoting host defense and immunopathologic processes. IFNγ exerts its pleiotropic effects on cells through an interaction with a specific high affinity receptor expressed at the cell surface. Functionally active receptors require the presence of two distinct species specific polypeptides: a 90 kDa α chain that is both necessary and sufficient for IFNγ binding and processing and necessary but not sufficient for biologic response induction, and a second recently cloned polypeptide now denoted as the IFNγ receptor β chain needed exclusively for development of functional responses in cells (Jung et al., 1987; Jung et al., 1990; Fischer et al., 1990; Farrar et al. 1991; Gibbs et al., 1991). Although the function of the receptor β chain remains entirely unclear, the structure-function relationships that exist within the receptor α chain have been the focus of a number of recent studies (Farrar et al., 1991; Farrar et al., 1992). Specifically, these analyses have revealed two topographically distinct, functionally important regions within the receptor α chain's intracellular domain. The first is comprised of 48 amino acids, proximal to the receptor's transmembrane domain (amino acids 256–303), and contains elements required for both receptor-mediated ligand internalization and biologic response induction (enhancement of MHC class I expression) (Farrar et al., 1991). The second region is located near the receptor's carboxy terminus, distal to the transmembrane region, and includes three closely spaced amino acids, Y440, D441, and H444, which are required exclusively for biologic responsiveness (Farrar et al., 1992).

The increased understanding of the structure and function of the IFNγ receptor has coincided with an explosive growth in understanding of the intracellular molecular events that underlie IFNγ dependent signal transduction. Recently IFNγ has been shown to induce in cells the phosphorylation and activation of a family of latent SH2 domain containing cytoplasmic transcription factors, such as the protein identified as p91. Activation of p91 effects the assembly of an active p91-containing multimolecular transcription factor complex which translocates to the nucleus and binds to specific sequences in the promoters of IFNγ inducible genes, thereby initiating gene transcription (Decker et al., 1991; Schindler et al., 1992; Fu et al., 1993; Shuai et al., 1993; Pearse et al., 1993). Although these observations have substantially enhanced the understanding of IFNγ signal transduction, they have not defined the molecular mechanisms coupling the IFNγ receptor to p91 activation.

IFNγ is also known to be a potent activator of monocytes and macrophages and is, therefore, a critical component for host defense and the inflammation response. The secretion of IFNγ elicits the induction of numerous genes that encode for proteins that can act as soluble, secreted mediators of inflammation, such as IL-8 and IP-10, and other receptor proteins that are crucial for immune responsiveness and host defense. IFNγ is, therefore, believed to contribute to the adverse effects of inflammatory diseases and autoimmune diseases because of its significant gene inducible characteristics. It would be advantageous, therefore, to identify a means for inhibiting the inducible gene transcription activity of IFNγ and thereby inhibit the activation of the IFNγ inducible genes and the resulting cellular response in a direct and specific manner. The identification of such a means would be useful as a therapeutic treatment for autoimmune and inflammatory diseases and for the treatment of cancer.

SUMMARY OF THE INVENTION

This invention encompasses novel compositions and methods that result in the inactivation of IFNγ inducible transcription factors by binding to the transcription factor in the cell and inhibiting the transcriptional activity of the factors. In one embodiment, a composition comprising an isolated peptide containing the amino acid sequence $Xaa_1$-Asp-$Xaa_2$-$Xaa_3$-His (SEQ ID NO:1) where $Xaa_1$ is a phosphorylated tyrosine and $Xaa_2$ and $Xaa_3$ are any amino acid, that is capable of specifically binding to the p91 family of IFNγ inducible transcription factors in a cell is provided. This amino acid sequence is based on residues 440–444 of the IFNγ receptor α chain. Other suitable peptides can be designed so long as they contain the 5 amino acid sequence of SEQ ID NO:1 and are capable of binding to a member of the p91 family of IFNγ inducible transcription factors. The specific binding activity of a phosphorylated peptide containing the peptide sequence of SEQ ID NO:1 was demonstrated by comparison with a non-phosphorylated peptide having the same sequence which showed little or no capacity to bind to a p91 transcription factor. Derivatives of these peptides can also be prepared that exhibit the functionality of being capable of binding to the transcription factor and inhibiting its transcriptional activity in a cell.

In another embodiment of the present invention, a method for inhibiting the intracellular activation of a transcription factor by introducing into a cell an effective amount of a peptide that contains the 5 amino acid sequence of SEQ ID NO:1, or a derivative thereof, which specifically binds to a transcription factor in the cell is also provided. The introduction of the exogenous peptide, or derivative thereof, into a cell causes the peptide to bind to the transcription factor and inhibit its transcriptional activity.

DETAILED DESCRIPTION OF THE INVENTION

Figure 1:
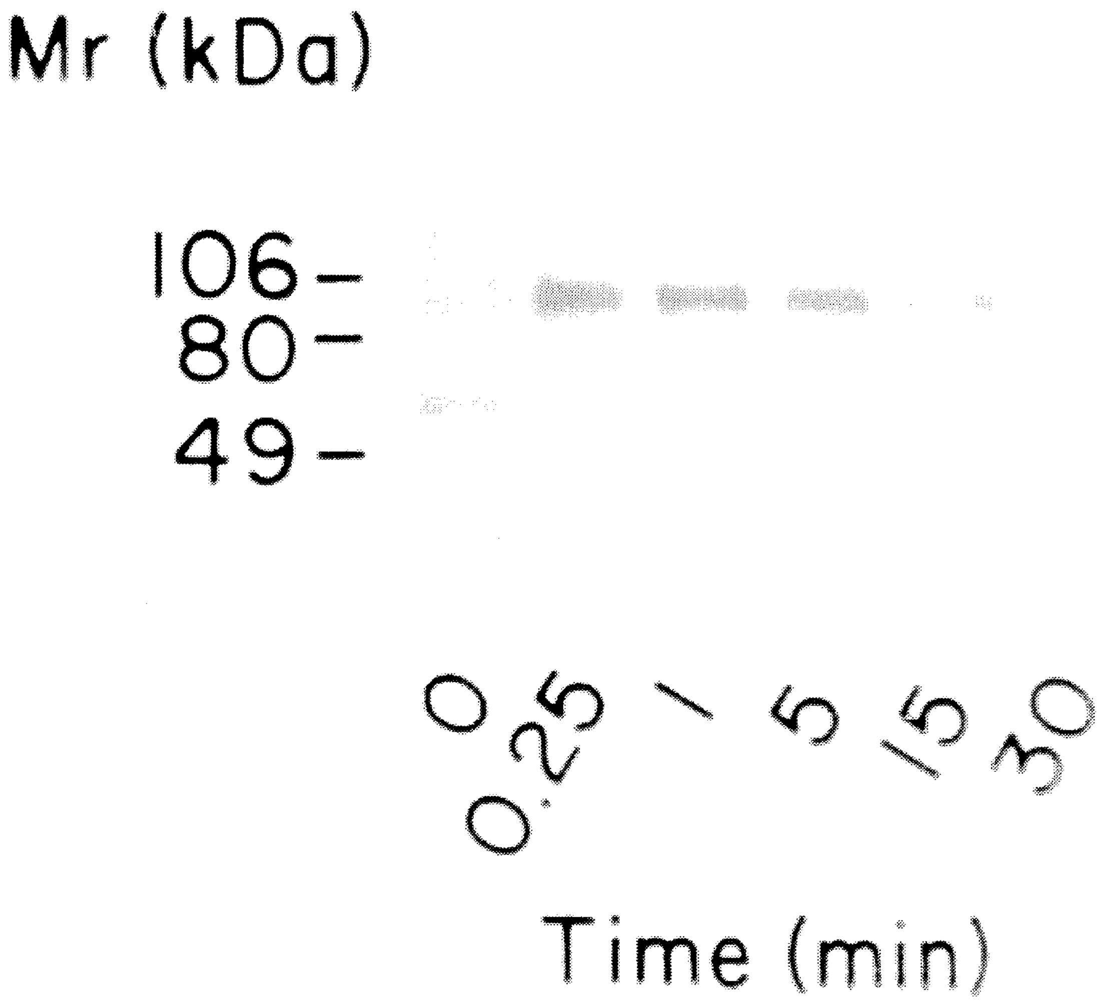
FIG. 1 is a western blot illustrating the kinetics of IFNγ receptor tyrosine phosphorylation.

In accordance with the present invention, it has been discovered that IFNγ inducible transcription factors can be inhibited by the introduction of a composition capable of binding to the transcription factor in the cell. In particular, this invention describes the heretofore unrecognized direct and specific interaction of a member of a family of proteins that exhibit transcriptional activation properties in response to IFNγ with a peptide derived from the IFNγ receptor α chain molecule. Although it had previously been shown that IFNγ induced the phosphorylation and activation of a cytoplasmic transcription factor, p91, the relationship between IFNγ, the IFNγ receptor, and the cytoplasmic transcription factor, was not known.

The composition of this invention comprises a peptide that includes a sequence of 5 amino acids that comprises a phosphorylated tyrosine linked to an aspartate residue, two amino acid residues that can be any amino acid, and a histidine residue, and can be denoted by $Xaa_1$-Asp-Xaa $_2$-$Xaa_3$-His. This amino acid sequence is identified as SEQ ID NO:1. It has been found that a peptide molecule having this sequence is capable of directly and specifically binding to the p91 transcription factor family and inhibiting its transcriptional activity in a cell. This 5 amino acid sequence corresponds to the sequence of amino acids 440–444 (Tyr-Asp-Lys-Pro-His, SEQ ID NO:2) of the IFNγ receptor molecule except that the tyrosine residue in the composition of the present invention is phosphorylated. By phosphorylating the tyrosine residue in the amino acid sequence of SEQ ID NO:2, it is possible to cause the specific binding of the phosphorylated peptide with the p91 transcription factor in the cell.

The novel peptides of the present invention may comprise a longer peptide than SEQ ID NO:1 by having more amino acids added to either of the terminal amino acids so long as the resulting peptide remains capable of binding to the transcription factor. Thus, amino acid sequences can be introduced at either end of the amino acid sequence of SEQ ID NO:1 and be considered within the scope of the present invention. Preferably, peptides prepared in accordance with this invention and useful for binding to a member of the p91 transcription factor family to inhibit its transcriptional activity are between five and about thirty amino acids in length. The peptide can be derived from the IFNγ receptor amino acid sequence or can be an unrelated sequence provided that the five amino acid sequence of SEQ ID NO:1 is included in the peptide or is similar to the sequence of SEQ ID NO:1 maintaining that the tyrosine in that amino acid sequence is phosphorylated. The tyrosine residue in a peptide sequence can by phosphorylated by known methods. The peptide can also be produced by standard synthetic procedures such as by "classical" Merrifield method of solid phase peptide synthesis or by using the FMOC strategy on a RAMPS multiple peptide synthesis system (DuPont Co., Wilmington Del.) as described in Caprino and Han (1972). Other exemplary peptides suitable for use in binding to p91 transcription factors include the ninemer Thr-Ser-Phe-Gly-$Xaa_1$-Asp-Lys-Pro-His, where $Xaa_1$ is phosphorylated tyrosine, identified as SEQ ID NO:3, or the dodecamer Thr-Ser-Phe-Gly-$Xaa_1$-Asp-Lys-Pro-His-Val-Leu-Val, where $Xaa_1$ is a phosphorylated tyrosine, identified as SEQ ID NO:4.

After a suitable peptide has been prepared, the peptide can be delivered to a cell by any known and available means. For example, the peptide can be modified to include specific transit peptides that are capable of delivering the peptide into a cell; the peptide may be conjugated with a carrier moiety such as liposome that is capable of delivering the peptide into a cell; or the peptide can be delivered directly into a cell by microinjection or by intravenous administration. An effective amount of the peptide must be introduced into the cell so that binding of the transcription factor takes place. It is to be understood that the amount of peptide necessary to be introduced into any particular cell is dependent upon the cell, but can be determined using standard dose/response analysis.

Based on the structural features of the critical amino acid sequence of the peptides of the present invention that permit the binding of the peptide with the transcription factor, one can develop non-peptidyl derivatives that are capable of binding to the p91 transcription factors. It is believed that at a minimum, non-peptidyl compositions that would be capable of binding transcription factors would contain a phosphorylated tyrosine-like structure and would be capable of being introduced into a cell.

The peptide prepared in accordance with the present invention can be used to inhibit the intracellular activation of IFNγ inducible transcription factors in a mammalian cell and thereby provide a useful therapeutic composition for use in the treatment of diseases defined by an uncontrolled immune response or inflammatory response such as autoimmune and inflammatory diseases. The peptide of the present invention may also be useful in the treatment of cancer by targeting the peptide to cancerous cells.

The following examples further describe the materials and methods used in carrying out the invention and are provided to illustrate the present invention and are not intended to limit the invention in any manner.

EXAMPLE 1

This example illustrates the discovery that IFNγ was capable of inducing tyrosine phosphorylation of its own receptor and that the tyrosine residue at amino acid position 440 of the IFNγ receptor was a specific phosphorylation substrate.

For these experiments, Colo-205, a human adenocarcinoma cell line obtained from the ATCC, was used because it was known to express a high number of IFNγ receptors (10,000 receptors/cell) and has been well characterized with regard to both biologic responsiveness to IFNγ and IFNγ receptor serine/threonine phosphorylation (Hershey and Schreiber, 1989; Hershey et al., 1990). Colo-205 cells ($5–10\times10^7$) were resuspended in one ml of PBS-10% FCS and were then incubated at 37° C., either in the presence or absence of rHuIFNγ (10,000IRU). Purified recombinant human IFNγ was provided by Dr. Susan Kramer of Genentech, Inc. (South San Francisco, Calif.). The rHuIFNγ used displayed specific antiviral activities of 3.8–$10^7$ IRU/mg. Purified rHuIFNγ was radioiodinated, using Bolton Hunter reagent (ICN Chemicals, Radioisotope Division, Irvine, Calif.) to specific activities of 6.5–17.8 μCi/μg as described in Celada et al. (1985). The reaction was stopped by adding 4 mls of ice-cold PBS. Cells were pelleted, washed once in ice-cold PBS, and then lysed in one ml of lysis buffer (25 mM Tris-HCl (pH 8.0), 1% NP-40, 150 mM NaCl 1 mM sodium orthovanadate, 10 mM NaF, 1 mM PMSF, 5 mM iodoacetamide, 10 mg/ml leupeptin and aprotinin). Solubilized cells were centrifuged at 15,000×g to remove cell nuclei and the supernatants were then incubated with 10 μg of GIR-94 for 30 minutes at 4° C. Protein G sepharose was added to the reaction mixture and the incubation continued for an additional 30 minutes. The beads were pelleted by centrifugation (10,000×g, for 3 minutes at 4° C.) and then washed 3 times with lysis buffer containing 1% SDS, 0.5% deoxycholate and 1% BSA and 2 times with PBS containing 1 mM sodium orthovanadate. Beads were resuspended in 50 μl of 2×laemmli buffer containing 180 mM β-mercaptoethanol, heated to 65° C. for 5 minutes, and pelleted by centrifugation. The supernatants were removed and one third of each sample used for western blotting with GIR-94 (anti-IFNγ receptor) while the remaining two thirds used for western blotting with murine $IgG_{2b}$ antiphosphotyrosine monoclonal antibody, 4G10, obtained from UBI (Lake Placid, N.Y.). Samples were loaded and electrophoresed on 4%–15% SDS-polyacrylamide gels (Biorad, Richmond, Calif.). Fractionated proteins were then transferred electrophoretically to nitrocellulose. Nitrocellulose membranes were blocked 1–18 hours at 4° C. in PBS containing 5% non-fat dry milk. The membranes were then washed with PBS-tween (0.05% tween-20) and incubated for one hour with either biotinylated GIR-94 or 4G10 (1 mg/ml). The membranes were then washed and incubated for 20 minutes in streptavidin-horseradish peroxidase and subsequently developed by chemiluminescence using Amersham's (Arlington Heights, Ill.) ECL western blotting system. The specificity of the phosphotyrosine antibody was confirmed by the ability of O-phospho-DL-tyrosine but not O-phospho-L-serine or O-phospho-L-threonine to block 4G10 from binding to the nitrocellulose bound receptor.

To determine the amount of receptor precipitated at each time point, aliquots from each immunoprecipitate were subjected to western blot analysis using a monoclonal antibody (GIR-94, a murine antibody $IgG_{2b}$) that is specific for the human IFNγ receptor extracellular domain. In the absence of added IFNγ, no tyrosine phosphorylated receptor was detected (FIG. 1, lane 1). However, following addition of IFNγ, a rapid and reversible phosphorylation of the receptor was observed. IFNγ receptor α chain phosphorylation reached maximum levels between 15 seconds and 1 minute after IFNγ addition (FIG. 1, lanes 2 and 3, respectively), remained at plateau levels through 5 minutes (lane 4), was significantly reduced at 15 minutes (lane 5) and approached background levels by 30 minutes (lane 6). IFNγ dependent tyrosine phosphorylation of the IFNγ receptor α chain was inhibited by pretreatment of the cells with herbimycin A (1 mM). Interestingly, this treatment also blocked IFNγ dependent MHC class II induction on these cells. The specificity of the 4G10 western blotting was confirmed by three criteria. First, detection of the tyrosine-phosphorylated receptor α chain was blocked if the 4G10 mAb was preincubated with phosphotyrosine but not with phosphoserine or phosphothreonine. Second, the same band was detected using another phosphotyrosine specific mAb (PY20). Third, the phosphorylated IFNγ receptor α chain could also be detected when 4G10 was used to immunoprecipitate phosphoproteins from lysates of IFNγ treated cells and western blot analysis performed using the IFNγ receptor specific GIR-94 monoclonal antibody.

These results thus demonstrate that IFNγ induced tyrosine phosphorylation of the IFNγ receptor α chain is an extremely rapid process and establishes that tyrosine phosphorylation of the IFNγ receptor α chain is the earliest response yet observed of cells to IFNγ.

To further characterize the tyrosine phosphorylation of the IFNγ receptor and to partially validate its biologic significance, concomitant dose-response phosphorylation and MHC class II induction analyses were performed. Colo-205 cells (1×$10^8$ cells/ml) were stimulated for 5 minutes with the indicated concentrations of rHuIFNγ as shown in FIG. 2. Cells were lysed and the IFNγ receptor immunoprecipitated, subjected to SDS-PAGE and electrophoretically transferred to nitrocellulose membranes as described above. Membranes were blotted with the mAb 4G10 (anti-phosphotyrosine) as described. Colo-205 cells (1×$10^8$ cells/ml) were also stimulated for 5 minutes with the indicated concentrations of rHuIFNγ, washed, and incubated an additional 48 hours in the absence of rHuIFNγ. MHC class II expression was quantitated by flow cytometric analysis.

Figure 2A:
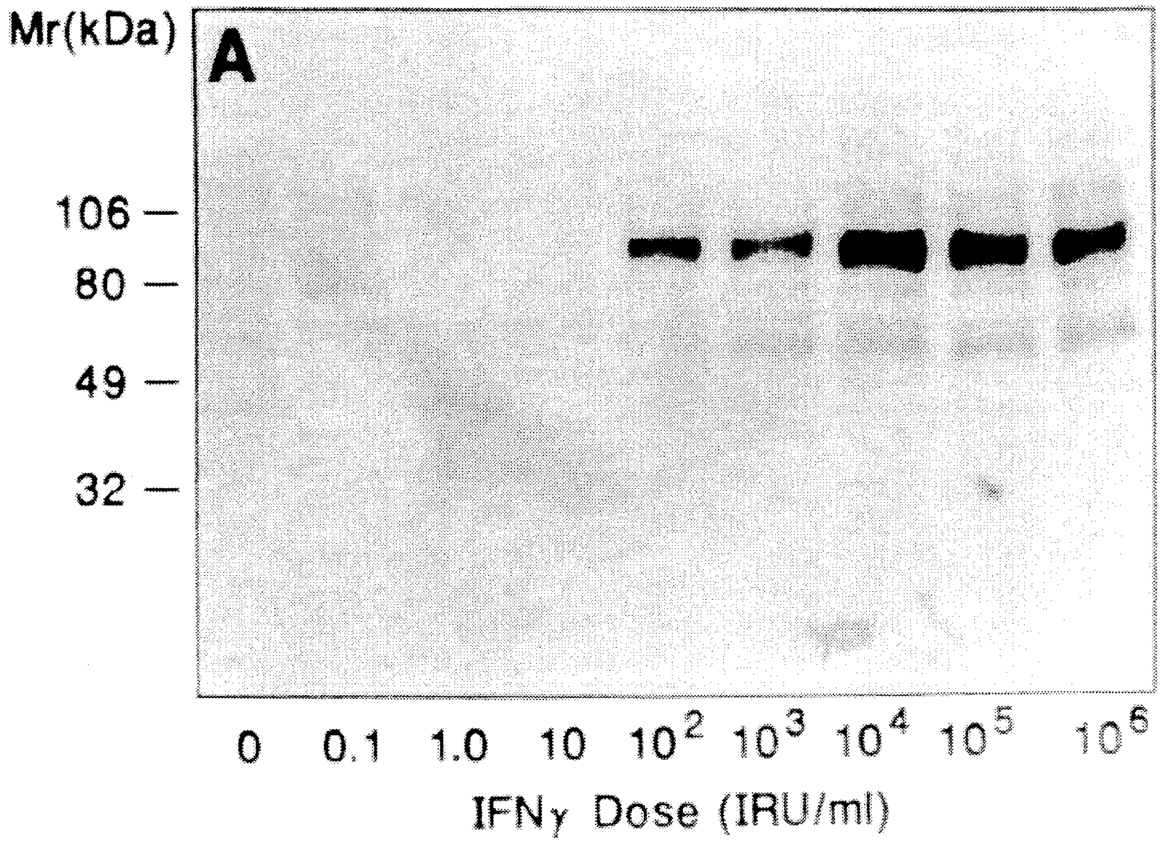
FIG. 2A is a western blot illustrating the dose response of receptor phosphorylation in response to IFNγ doses.
Figure 2B:
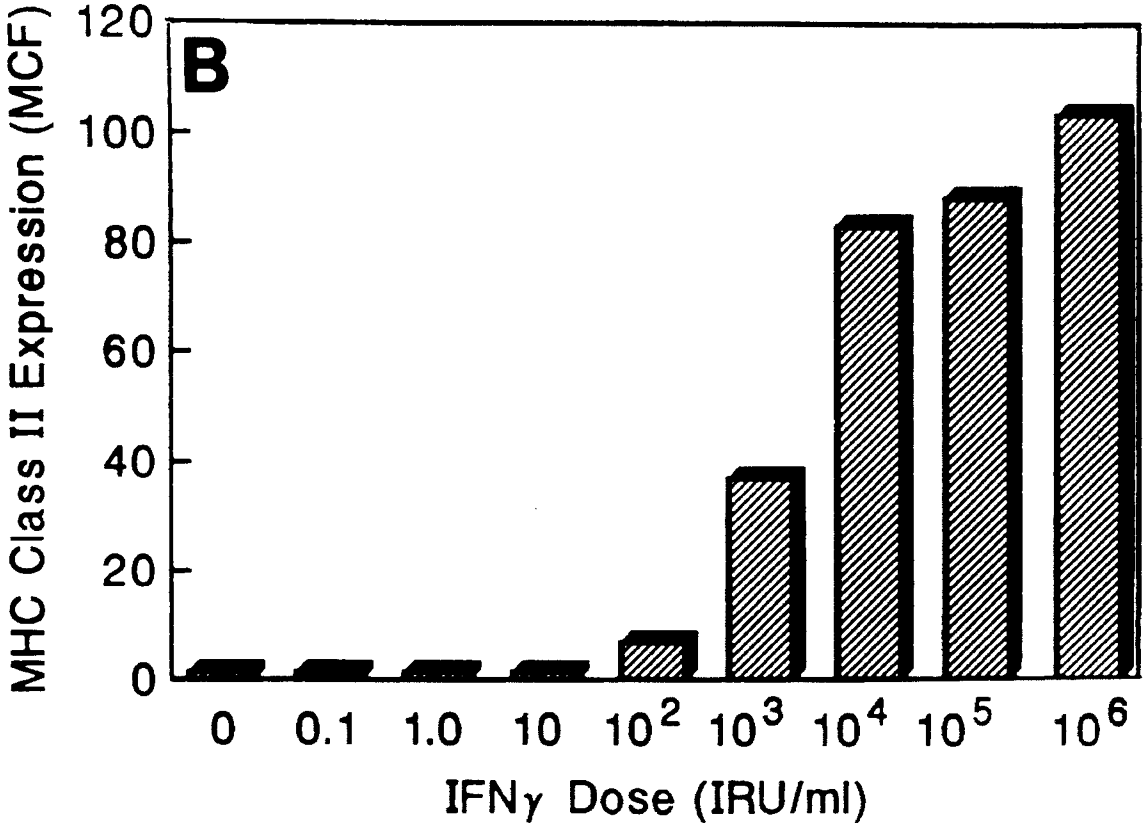
FIG. 2B is a graphical representation of the kinetics of MHC class II induction analyses in response to IFNγ doses.

IFNγ receptor tyrosine phosphorylation was detected when $10^8$ Colo-205 were treated for 5 minutes with 100 IRU/ml of IFNγ and reached maximal levels at IFNγ doses of 10,000 IRU/ml (FIG. 2A). A similar profile was obtained for the induction of an IFNγ biologic response in these cells (MHC class II induction) when Colo-205 were exposed to identical doses of IFNγ for 5 minutes, washed and then placed back in culture for 48 hours to allow time for the biologic response to develop (FIG. 2B). Thus, the amount of IFNγ required to induce IFNγ receptor tyrosine phosphorylation parallels that required to induce biologic responses.

EXAMPLE 2

This example illustrates the requirement of the presence of the species-specific receptor β chain for IFNγ dependent tyrosine phosphorylation of the IFNγ receptor α chain.

Figure 3A:
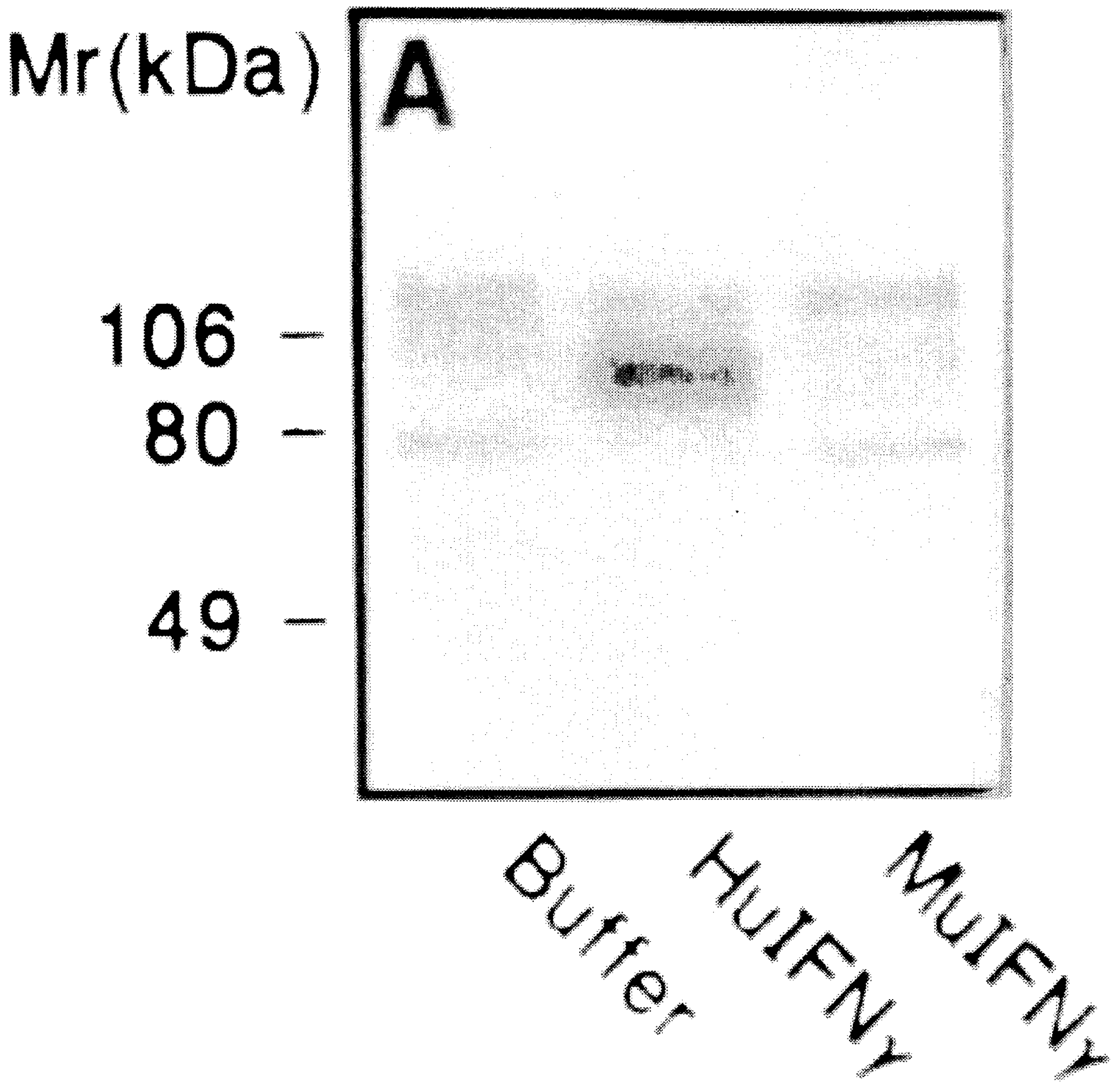
FIG. 3 is series of western blots illustrating that the IFNγ receptor a chain requires the presence of the species-specific receptor α chain for IFNγ dependent tyrosine phosphorylation.
Figure 3B:
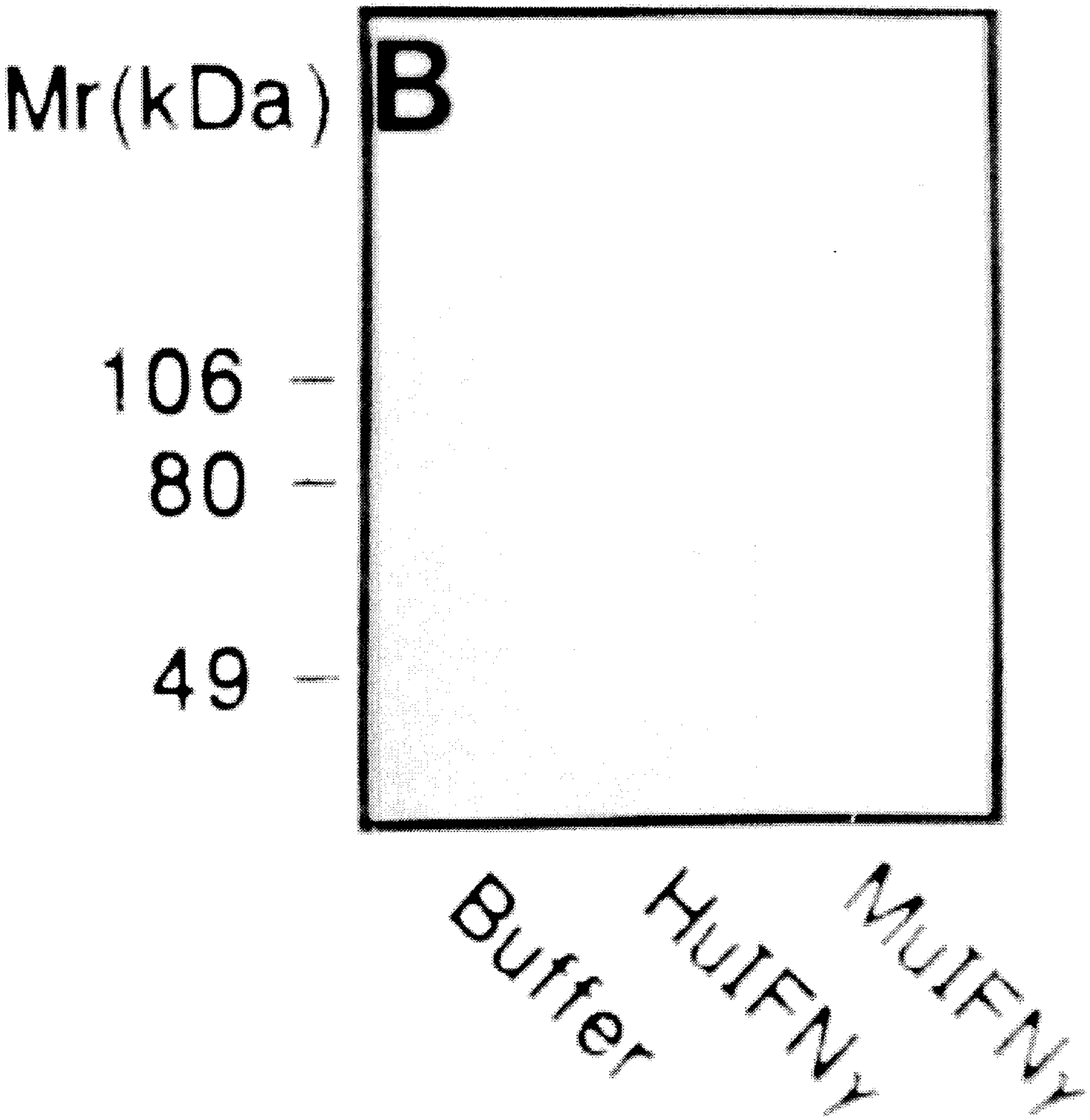
Figure 3C:
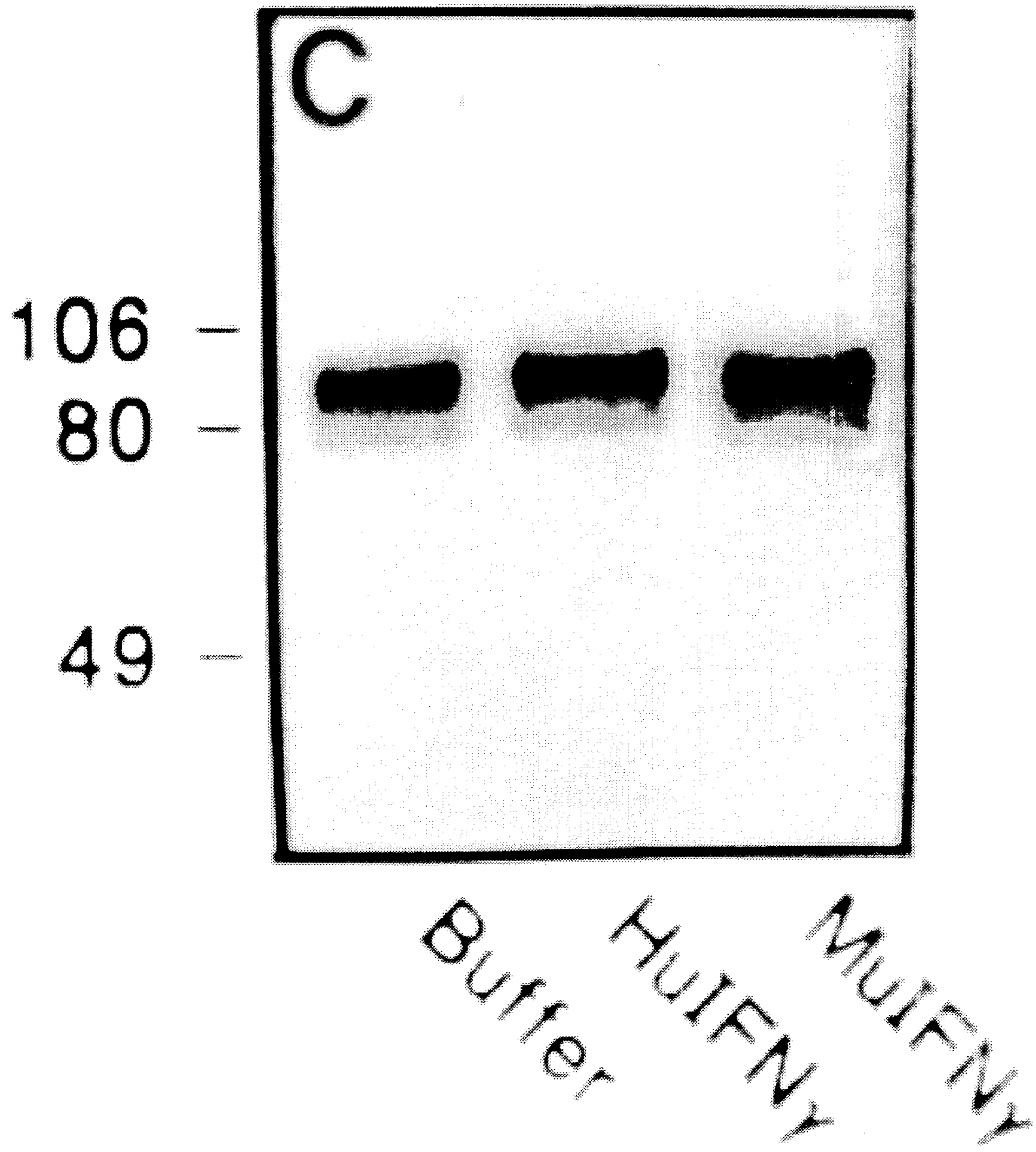
Figure 3D:
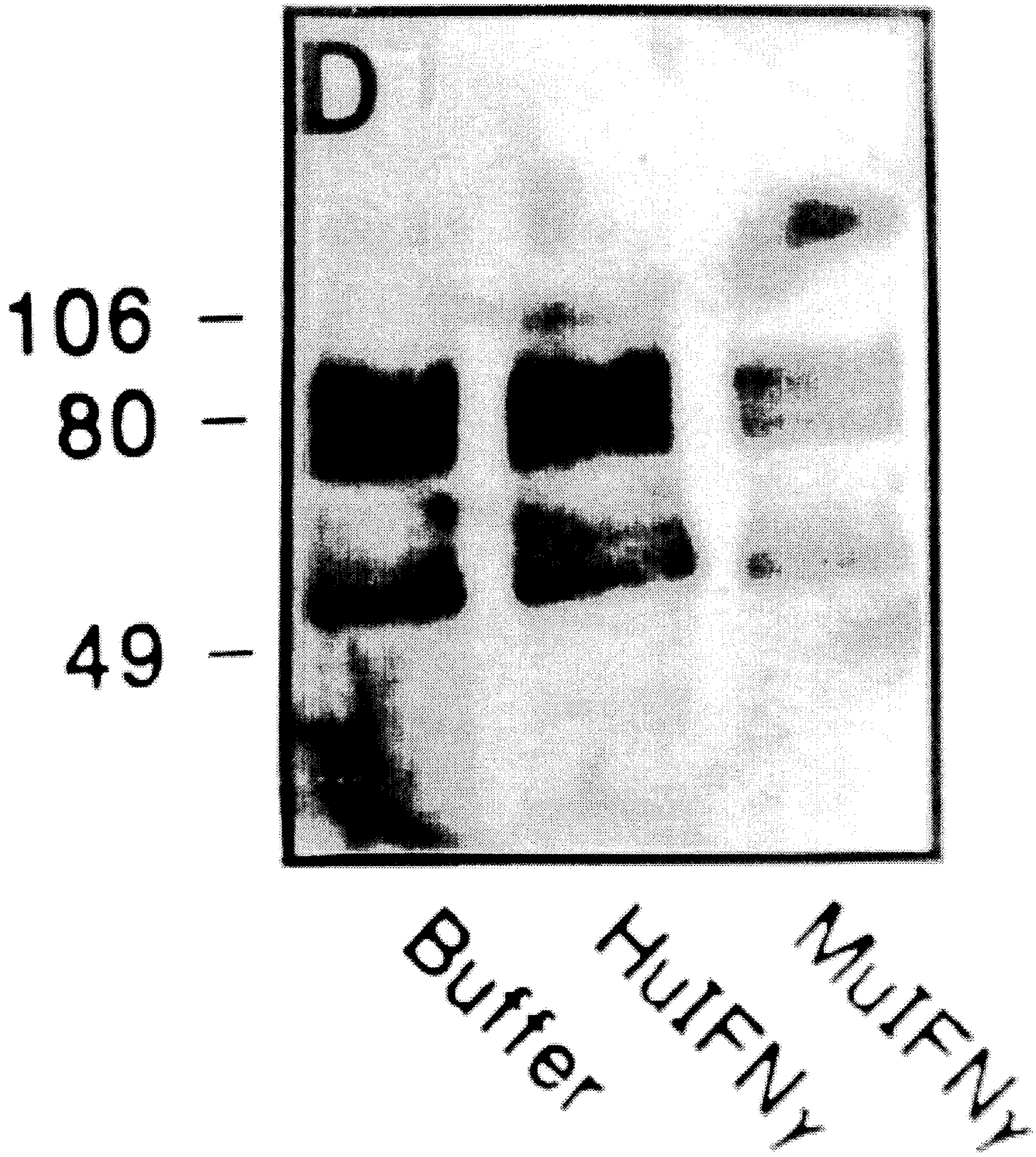

Cellular responsiveness to IFNγ requires the presence of both species matched receptor α and β polypeptide chains (Jung et al., 1987; Jung et al., 1990; Fischer et al., 1990; Farrar et al., 1991; Gibbs et al., 1991; Hemmi et al., 1992). To determine whether a similar requirement is shown for IFNγ induced IFNγ receptor tyrosine phosphorylation, a Colo-205 cell line that stably expressed the murine IFNγ receptor α chain designated M-Colo.22 (Hershey et al., 1990) was utilized. On these cells, the transfected murine receptor α chain binds and processes murine IFNγ in a normal manner but is unable to support biologic responses (such as MHC class II induction) to murine IFNγ. M-Colo.22 cells were incubated with buffer (lane 1 and 4), rHuIFNγ (10,000 IRU/ml) (lane 2 and 5), or rMuIFNγ (10,000 IRU/ml) (lane 3 and 6) for 5 minutes at 37° C. Cells were lysed and the human IFNγ receptors (Panel A and C of FIG. 3) or murine IFNγ receptors (Panel B and D of FIG. 3) were immunoprecipitated using the mAb GIR-94 or polyvalent goat anti-murine IFNγ receptor immune sera, respectively. Immunoprecipitates were subjected to SDS-PAGE and electrophoretically transferred to nitrocellulose membranes as previously described. Human IFNγ receptor (Panel A and C of FIG. 3) and murine IFNγ receptor (Panel B and D of FIG. 3) immunoprecipitates were blotted with the mAbs 4G10 (anti-phosphotyrosine) (Panel A and B), GIR-208 (anti-human IFNγ receptor) (Panel C), or GR-20 (anti-murine IFNγ receptor) (Panel D). As shown in FIG. 3, treatment of M-Colo.22 for 5 minutes at 37° C. with 10,000 IRU/ml of human IFNγ resulted in tyrosine phosphorylation of the endogenous human IFNγ receptor (FIG. 3A, lane 2) but not the transfected murine IFNγ receptor (FIG. 3B, lane 5). Stimulation of cells with murine IFNγ did not result in tyrosine phosphorylation of either the human or murine IFNγ receptors (FIG. 3A and 3B, lanes 3 and 6, respectively). The cell line expressed equivalent levels of both the human and murine receptor α chains as documented by immunoprecipitation and western blot analyses using monoclonal antibodies specific for each species of receptor α chain (FIG. 3, panels C and D). These results demonstrate that the species specific IFNγ receptor β chain is required for the IFNγ induced tyrosine phosphorylation of the IFNγ receptor α chain.

EXAMPLE 3

This example is provided to illustrate that the functionally critical carboxy terminal region of the IFNγ receptor α chain is not required for tyrosine kinase activation but is a target for tyrosine phosphorylation.

The complete nucleotide and amino acid sequence of the IFNγ receptor α chain is known and described in Aguet et al. (1988), the entirety of which is hereby incorporated by reference hereto. Although there are five tyrosine residues within the intracellular domain of the IFNγ receptor α chain (Aguet et al., 1988), only one (Y440) is functionally important (Farrar et al., 1992). Therefore, the issue of whether Y440 is required for tyrosine kinase activation or is a substrate for the activated kinase was analyzed. This issue was addressed using a family of human chromosome 21 containing murine fibroblasts (SCC16-5 which is a murine fibroblast cell line that contains a single copy of human chromosome 21 as described in Janssen et al. (1986) and WA-17 which is a murine L cell line that contains three copies of human chromosome 21 as described in Raziuddin et al., (1984)) that were transfected to stably express either the wild type human IFNγ receptor α chain, a human receptor α chain containing a point mutation in which Y440 was replaced by phenylalanine (referred to as YF440), or a third α chain mutant in which all the intracellular domain tyrosine residues except Y440 were replaced by phenylalanine (designated 4XYF). The mutant IFNγ receptor α chains designated YF440 and 4XYF were produced by the PCR method. The tyrosine to phenylalanine mutation in YF440 was introduced in one strand of the native IFNγ receptor α chain by PCR utilizing primer #482019 which has the sequence 5'CCTCCTTTGGTTTTGATAAAC-3' (SEQ ID NO: 5) and an IFNγ receptor a chain downstream oligonucleotide that is 3' to Y440. The resulting PCR cDNA product contained the tyrosine to phenylalanine mutation and was isolated. A second PCR reaction was conducted in a similar manner utilizing oligonucleotide primer #491066 which has the sequence 5'-GTTTATCAAAACCAAAGGAGG-3' (SEQ ID NO:6) and an IFNγ receptor α chain upstream primer sequence that is 5' to Y440 to introduce the tyrosine to phenylalanine mutation into the complementary DNA strand. The resulting PCR cDNA product contained the tyrosine to phenylalanine mutation and was isolated. The two PCR products were then permitted to anneal in the area of complementarity and a third PCR reaction was conducted using other oligonucleotides corresponding to the 5' and 3' ends of the IFNγ receptor α chain to generate a full length mutant sequence. This PCR product was then digested with SacI and ClaI which provided a fragment containing the F440 mutation and purified. This fragment was introduced into pBluescript which contained the native IFNγ receptor sequence, but which had been cleaved with ClaI and SacI to remove the region therebetween which contained Y440. The resulting mutant IFNγ receptor was cloned into pSFFV for expression and subsequent transfection. Using a similar PCR procedure, the mutant designated 4XYF was produced by sequential introduction of tyrosine to phenylalanine mutations at amino acid positions 287, 294, 380 and 462 using the following oligonucleotide PCR primers, respectively, to introduce the desired mutation:

For YF287, 294:

Primer #000001

5'TGTATCACTCATCACGTCATTCCAGC-CATTTTCGTTAGAAAAGG 3' (SEQ ID NO:7)

and

Primer #000002

5'ATGACGTGATGAGTGATACAAATTTTGATTC (SEQ ID NO:8)

For YF380:

Primer #000003

5'GCTTTGAACTCGTTTCAATACAG 3' (SEQ ID NO:9)

and

Primer #000004

5'CTGGAGTGAAACGAGTTCAAAGCGATG 3' (SEQ ID NO:10)

For YF462:

Primer #000005

5'CCATCGATGTCATGAAAATTCTTTG-GAATCTTCTGTTGGTCTAAAACCAATC3' (SEQ ID NO:11)

Cells were transfected with all three constructs using the calcium phosphate precipitation method as described in Farrar et al. (1992). Cells transfected with all three constructs expressed comparable levels of each receptor form and bound and internalized IFNγ in a manner that was indistinguishable from native receptors on normal human cells. All three cell lines responded to homologous murine IFNγ indicating that the general class I MHC induction pathway was intact. Furthermore, the cell lines responded to IFNα2α indicating that they still contained human chromosome 21 and hence maintained expression of the human receptor β chain. However, only the cell lines that expressed wild type receptor α chain and the 4XYF mutant responded to human IFNγ while the YF440 mutant expressing cell line did not. This observation again reinforced the earlier finding that Y440 was the only functionally critical tyrosine residue within the receptor α chain's intracellular domain.

The three transfected cell lines were then tested for their capacity to phosphorylate IFNγ receptor tyrosine residues in response to human IFNγ. For each cell line, human receptor α chain phosphorylation in buffer- and IFNγ-treated cells was studied by western blotting using 4G10 and human IFNγ receptor α chain expression confirmed by western blotting with GIR-94. Cells were stimulated with IFN 10,000 units/ml for 30 seconds, lysed, human IFNγ receptors immunoprecipitated, immunoprecipitates were subjected to SDS-PAGE, electrotransferred to nitrocellulose, and immunoblotted with GIR-94 or 4G10.

Figure 4:
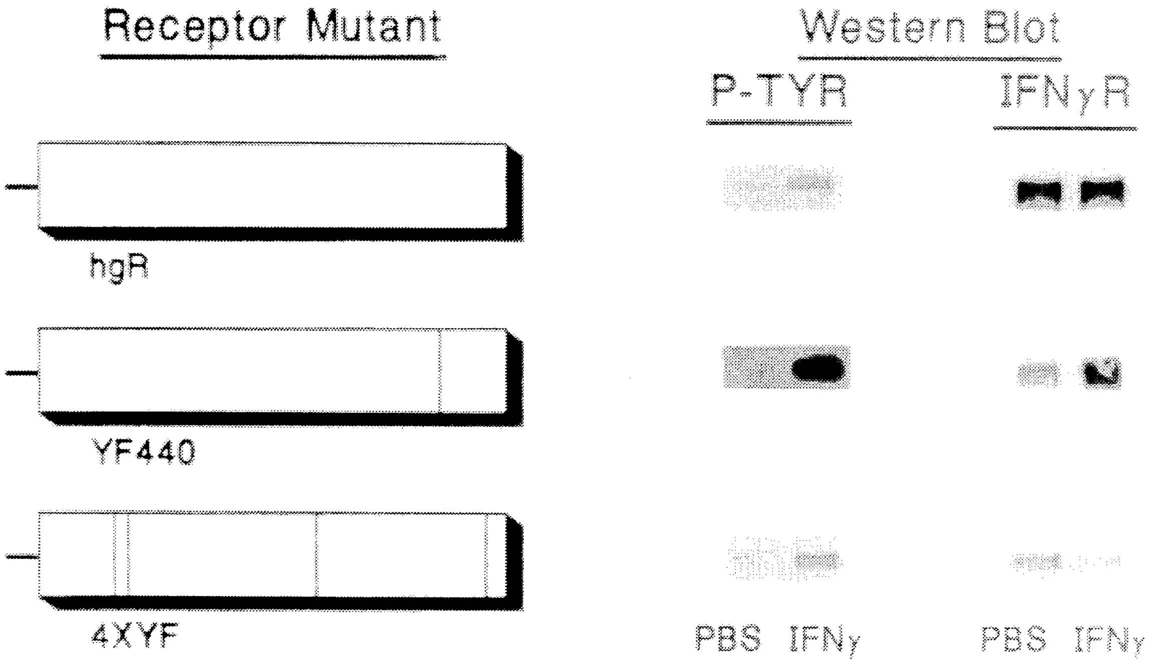
FIG. 4 is a graphical illustration and the corresponding western blot results of WA.17 expressing the wildtype human IFNγ receptor, WA.17 expressing the biologically inactive YF440 mutant IFNγ receptor, and SCC.16 expressing the biologically active IFNγ receptor containing the mutations YF287, YF294, YF380, YF462.

The cell line expressing wild type human IFNγ receptor α chain showed an IFNγ dependent receptor tyrosine phosphorylation response (FIG. 4, top panel). This result documented that IFNγ dependent IFNγ receptor tyrosine phosphorylation could be detected in transfected human chromosome 21 containing murine fibroblasts just as described above for authentic human cells. Interestingly, stimulation of cells expressing the YF440 mutant with human IFNγ also resulted in human receptor α chain tyrosine phosphorylation (FIG. 4, middle panel). This result indicated that either Y440 was not the target of the IFNγ inducible tyrosine kinase activity or that multiple tyrosine residues were phosphorylated following stimulation with ligand. This issue was resolved by the finding that the cell line that expressed the 4XYF mutant that contained only the single functionally important Y440 residue was indeed phosphorylated in response to IFNγ (FIG. 4, bottom panel). These results thus demonstrate that whereas the functionally critical Y440 residue is not required for tyrosine kinase activation, it is nevertheless a target for the activated enzyme.

EXAMPLE 4

This example is provided to illustrate that the phosphorylation of Y440 is required for IFNγ receptor signal transduction and that a phosphorylated IFNγ receptor derived peptide can inhibit the generation of active p91 transcription factor activity.

For this example, the finding that the latent IFN inducible transcription factor, p91, can be activated by IFNγ in a cell free system (Igarashi et al., 1993) was utilized to determine the biologic significance of the IFNγ induced tyrosine phosphorylation of the Y440 residue in the IFNγ receptor molecule. Colo-205 homogenates were stimulated with 1900 IRU of human IFNγ and p91 activation monitored using an electrophoretic mobility gel shift assay (EMSA) that employed a $^{32}$P-labeled 18 bp probe derived from the FcγR I gene promoter (Pearse et al., 1993). The EMSAs were carried out essentially as described (Igarashi et al., 1993). The oligonucleotide probe was based on the 3'18 base pairs of the Gamma Response Region (GRR) of the FcγRI gene (Pearse et al., 1993). Top strand: 5'-ATGTATTTCCCAGAAA-3' (SEQ ID NO: 12); Bottom strand: 5'-CTTTTCTGGGAAATA-3' (SEQ ID NO:13). The double stranded oligonucleotide was labeled by filling in the overhanging ends with dATP α $^{32}$P using the klenow large fragment (Boehringer Mannheim, Indianapolis, Ind.). Assays were performed using 5 μg of extract and 25,000 cpm (approximately 1 ng) of the double stranded $^{32}$P labeled GRR probe incubated in 10 mM Tris-HCl (pH7.5), 100 mM KCl, 5 mM $MgCl_2$, 1 mM DTT, 10% glycerol and 4 μg poly(dIdC) (dIdC) (Pharmacia) for 20 minutes at room temperature. The reactions were then electrophoresed through a 6% polyacrylamide gel in 0.25× TBE for 3 hours at 150 V. Gels were dried and subsequently analyzed by autoradiography. Supershifts were performed using antisera to the C-terminus of human p91 (Schindler et al., 1992) at a dilution of 1:100. Specificity of interactions were determined by the addition of 350 ng of the unlabeled GRR probe or 560 ng of the unlabeled 41 base pair double stranded oligonucleotide containing the ISRE of ISG15 (5'-GATCCATGCCTCGGGAAAGGGAAACCGAAACTGAAGCCAC-3' SEQ ID NO: 14) (David and Larner, 1992).

Colo-205 homogenates were prepared essentially as previously described (Igarashi et al., 1993). Briefly, 2×10$^8$ Colo-205 cells were washed in PBS and resuspended in 1 ml of reaction buffer containing 100mMHepes (pH 7.4), 20 mM $MgCl_2$, 100 mM NaCl, 200 μM ascorbic acid, 4 mM ATP, 2 mM EGTA, 1 mM PMSF, 10 μg/ml leupeptin and aprotinin. Cells were disrupted in a steel dounce until no intact cells remained. Colo-205 homogenates were diluted to 6.5 mg/ml in reaction buffer and 50 μl aliquots were incubated at 4° C. for 1 hour either in the absence or presence of 5 μl of specific peptides diluted in water. After the preincubation period with peptide, homogenates were incubated for 5 minutes at 37° C. with 1900 IRU of rHuIFNγ added in 5 μl of reaction buffer. The reactions were stopped by the addition of 0.45 ml of stop buffer consisting of 20 mM Hepes (pH 7.4), 1 mM $MgCl_2$, 10 mM KCl, 20% glycerol, 500 μM DTT, 0.1% NP-40, 1 mM PMSF, 10 μg/ml leupeptin and aprotinin. Homogenates were vortexed for 5 seconds and nuclei pelleted by centrifugation at 16,000×g for 5 minutes. The supernatant was then assayed for activation of p91 by electrophoretic mobility shift assay (EMSA). The results of the EMSA are shown in FIG. 5 and the material introduced into the respective lanes as follows:lane 1—Minus IFNγ, lane 2—Plus IFNγ, lane 3—unlabeled GRR, lane 4—unlabeled ISRE, lane 5—Plus Rabbit anti- p91, lane 6—Plus Normal Rabbit Serum, lane 7—83 μM TSFGYDKPH (Thr-Ser-Phe-Gly-Tyr-Asp-Lys-Pro-His, SEQ ID NO:15), lane 8—83 μM TSFGY-PO4DKPH (SEQ ID NO:3), lane 9—17 μM TSFGY-PO4DKPH (SEQ ID NO:3), lane 10—3 μM TSFGY-PO4DKPH (SEQ ID NO:3), lane 11—0.7 μM TSFGY-PO4DKPH (SEQ ID NO:3), lane 12—0.1 μM TSFGY-PO4DKPH (SEQ ID NO:3), lane 13—83 μM TSFGY-PO4AKPA (Thr-Ser-Phe-Gly-Xaa-Ala-Lys-Pro-Ala, where Xaa is phosporylated tyrosine, SEQ ID NO:16), lane 14—83 μM SLIGY-PO4RPTEDSK (Ser-Leu-Ile-Gly-Xaa-Arg-Pro-Thr-Glu-Asp-Ser-Lys, where Xaa is phosphorylated tyrosine, SEQ ID NO:17).

Figure 5:
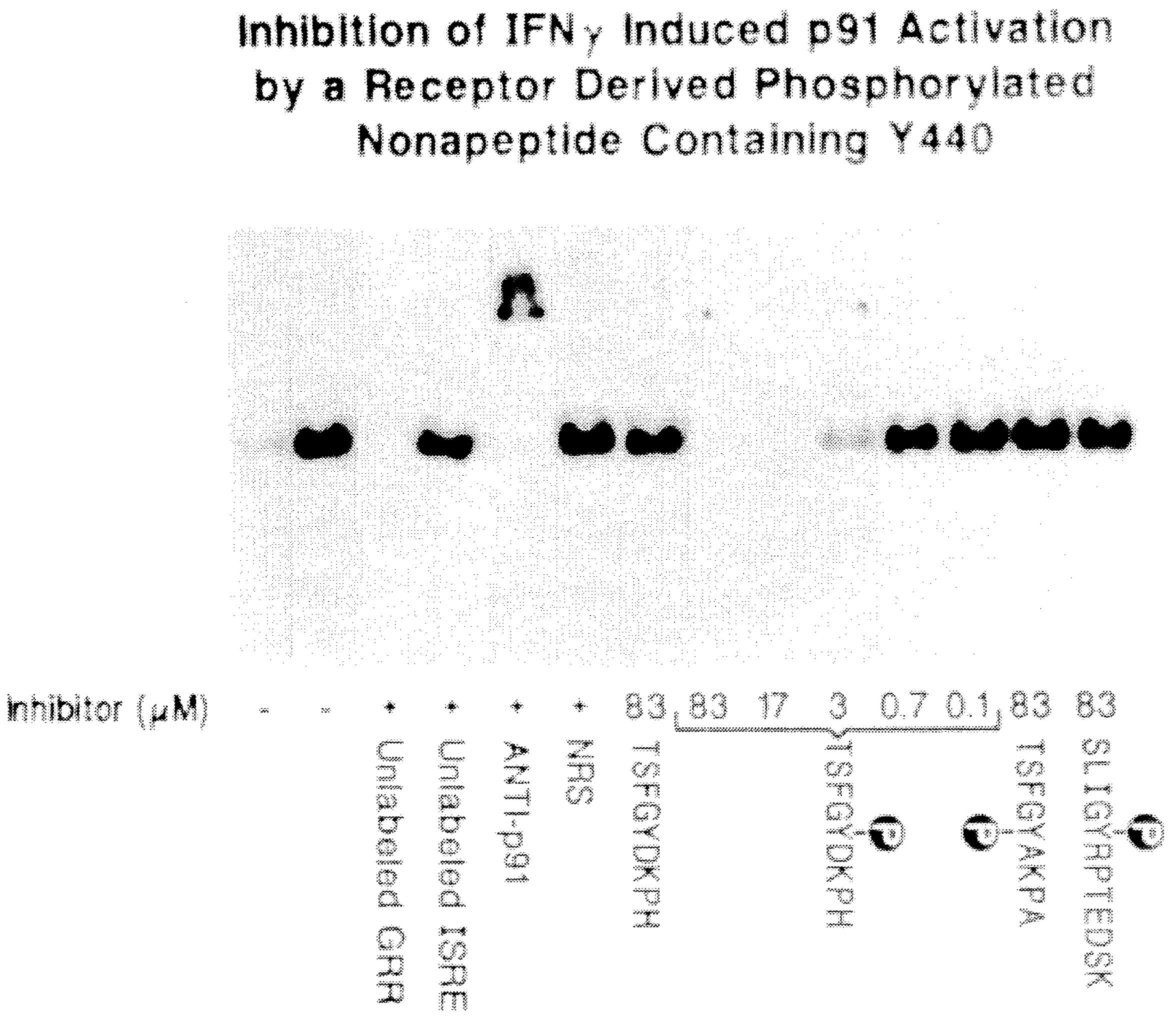
FIG. 5 is a photograph of the results of an electrophoretic mobility shift assay identifying that the peptide containing the amino acid sequence of SEQ ID NO:1 with phosphorylated tyrosine blocks the association or activation of the transcription factor p91 with the $^{32}P$ labeled oligonucleotide probe.

In the absence of IFNγ, no activated p91 was observed (FIG. 5, Lane 1). In contrast, addition of human IFNγ to the homogenate resulted in the generation of a prominent retarded band (Lane 2). The specificity of the retardation was confirmed by demonstrating that the unlabeled oligonucleotide probe inhibited the formation of the band (Lane 3) while an unlabeled oligonucleotide probe corresponding to the ISRE of ISG15 (David and Larner, 1992) did not (Lane 4). The presence of p91 in the gel shift complex was demonstrated using a rabbit antiserum specific for the carboxy terminal portion of human p91 (Schindler et al., 1992). Whereas anti-p91 serum effected a supershift of the transcription factor complex when added to the reaction mixture following addition of labeled probe (Lane 5), normal rabbit serum was without effect (Lane 6). These results thus validate the EMSA system and establish that p91 can be activated by ligand in homogenates of Colo-205.

To explore the role of Y440 in p91 activation, a series of 9- and 12-amino acid peptides based on sequences from the IFNγ receptor intracellular domain were generated. The peptides: TSFGYDKPH (SEQ ID NO:15), TSFGY-$PO_4$DKPH (SEQ ID NO:3), TSFGY-$PO_4$AKPA (SEQ ID NO:16), SLIGY-$PO_4$RPTEDSK (SEQ ID NO:17), Biotin-TSFGYDKPHVLV (Thr-Ser-Phe-Gly-Tyr-Asp-Lys-Pro-His-Val-Leu-Val, SEQ ID NO:18), Biotin-TSFGY-$PO_4$AKPAVLV (SEQ ID NO:4), Biotin-TSFGY-$PO_4$AKPAVLV (Thr-Ser-Phe-Gly-Xaa-Ala-Lys-Pro-Ala-Val-Leu-Val, where Xaa is phosphorylated tyrosine, SEQ ID NO:19), Biotin-SLIGY-$PO_4$RPTEDSK (SEQ ID NO:17) were synthesized manually using the FMOC strategy on a RAMPS™ multiple peptide synthesis system (DuPont Co., Wilmington, Del.) (Caprino and Han, 1972). After addition of phosphotyrosine residues, 35% piperidine/DMF was used to remove the FMOC groups. For the dodecapeptides, biotin groups were added to the amino terminus of the peptides.

Briefly, a five fold molar excess of biotinamidocaproate N-hydroxysuccinimide ester was suspended in 3 ml DMSO containing 1% N-methylmorpholine and added to the cartridge containing resin-linked peptide after the final FMOC removal. The slurry was rocked 2 hours, washed 3× in DMF, 3× in MeOH and then an Isatin test was performed to monitor completion of coupling. All peptides, phosphorylated and non-phosphorylated, were cleaved and deprotected according essentially to the protocol of E. A. Kitas et al. (1993). The resin-linked peptides were treated with 5 ml of 12.9% bromotrimethylsilane, 11.8% thioanisol, 75% trifluoroacetic acid (TFA), and 0.8% m-cresol for 16 hours at 4° C. Peptides were precipitated with tert-butyl methyl ether, redissolved in TFA, and subsequently precipitated and washed 5× with ether, resuspended in water, and lyophilized. Analytical reverse phase HPLC was performed and a single major peak was observed for each peptide. Electrospray mass spectrometry was performed on unfractionated peptides and a single moiety was detected with the predicted molecular mass for each of the peptides. Amino acid composition was verified and molarity calculated using a Beckman 6300 amino acid analyzer.

The peptides were preincubated with Colo-205 homogenates 30–60 minutes before addition of human IFNγ in the EMSA. Pretreatment with a peptide corresponding to residues 436–444 of the human IFNγ receptor α chain (TSFGYDKPH, SEQ ID NO:15) had no effect on p91 activation even when used at a final concentration of 83 μM (FIG. 5, Lane 7). In contrast, pretreatment with a phosphotyrosine containing nonapeptide with the same sequence blocked the activation of p91 in a dose dependent manner (FIG. 5, Lanes 8–12). Formation of an activated p91-labeled probe complex was completely inhibited at phosphopeptide inputs of 83 and 15 μM and 61% inhibited at phosphopeptide concentrations of 3 μM. Lower concentrations of the phosphorylated ninemer (0.7 and 0.1 μM) were not inhibitory. The specificity of the inhibition was confirmed using two additional phosphopeptides. First, no inhibition was noted when a mutated 436–444 phosphopeptide was used in which the functionally critical D441 and H444 residues were changed to alanine (Lane 13). Second, no inhibition was noted when a phosphorylated 12 amino acid peptide was used that was based on an IFNγ receptor α chain intracellular domain sequence (residues 458–469) that contains a functionally unimportant tyrosine residue (Y462) (Lane 14). These results thus suggest that the Y440 based phosphopeptide blocks the association of the IFNγ receptor with specific signaling effector molecules and thereby suggests that phosphorylation of Y440 is a critical event in IFNγ signal transduction.

EXAMPLE 5

This example is provided to illustrate that p91 interacts directly with a phosphorylated tyrosine containing five amino acid sequence comprising SEQ ID NO:1.

Different biotinylated 12 amino acid peptides that contained either tyrosine or phosphotyrosine were incubated with Colo-205 homogenates and examined whether p91 could be coprecipitated with biotinylated peptide using Steptavidin-Agarose. Homogenates from $4\times10^8$ Colo-205 cells were diluted to 15 mg/ml with reaction buffer. 0.5 ml aliquots (approximately $2.5\times10^7$ cell equivalents) were incubated either in the presence of or absence of 23000 IRU of IFNγ for 5 minutes at 37° C. Reactions were stopped by addition of 2.5 ml of stop buffer supplemented with 1 mM sodium orthovanadate and 1 mM EDTA, vortexed 5 seconds and centrifuged 5 minutes at 13,000 rpm. The supernatants were then incubated with the various biotinylated peptides at a final concentration of 2 μM at 4° C. for 1.5 hours. 175 μl of streptavidin-sepharose (Pierce, Rockford, Ill.) was then added and the incubation continued for an additional 1.5 hours. The sepharose was pelleted and washed 5× with 20 mM Hepes (pH 7.4), 150 mM NaCl, 0.5% NP-40, 5% glycerol, 1 mM $MgCl_2$, 500 μM DTT, 1 mM PMSF, 10 μg/ml leupeptin and aprotinin, 1 mM iodoacetamide, 1 mM EDTA, and 1 mM sodium orthovanadate. 40 μl of 2× laemmli buffer was added and samples placed at 75° C. for 5 minutes then electrophoresed on 4–15% SDS -polyacrylamide gels (Biorad). After transfer to nitrocellulose, membranes were blocked in 2.5% non-fat dry milk in 10 mM Tris-HCl (pH 8.0), 150 mM NaCl, 0.05% tween-20. Membranes were washed in the above described buffer without non-fat dry milk and then incubated with a 1:5500 dilution of rabbit antisera directed against the C-terminus of human p91. Membranes were then incubated with a 1:7500 dilution of peroxidase-conjugated goat anti-rabbit IgG (United States Biochemicals) and detected using ECL (Amersham).

Figure 6A:
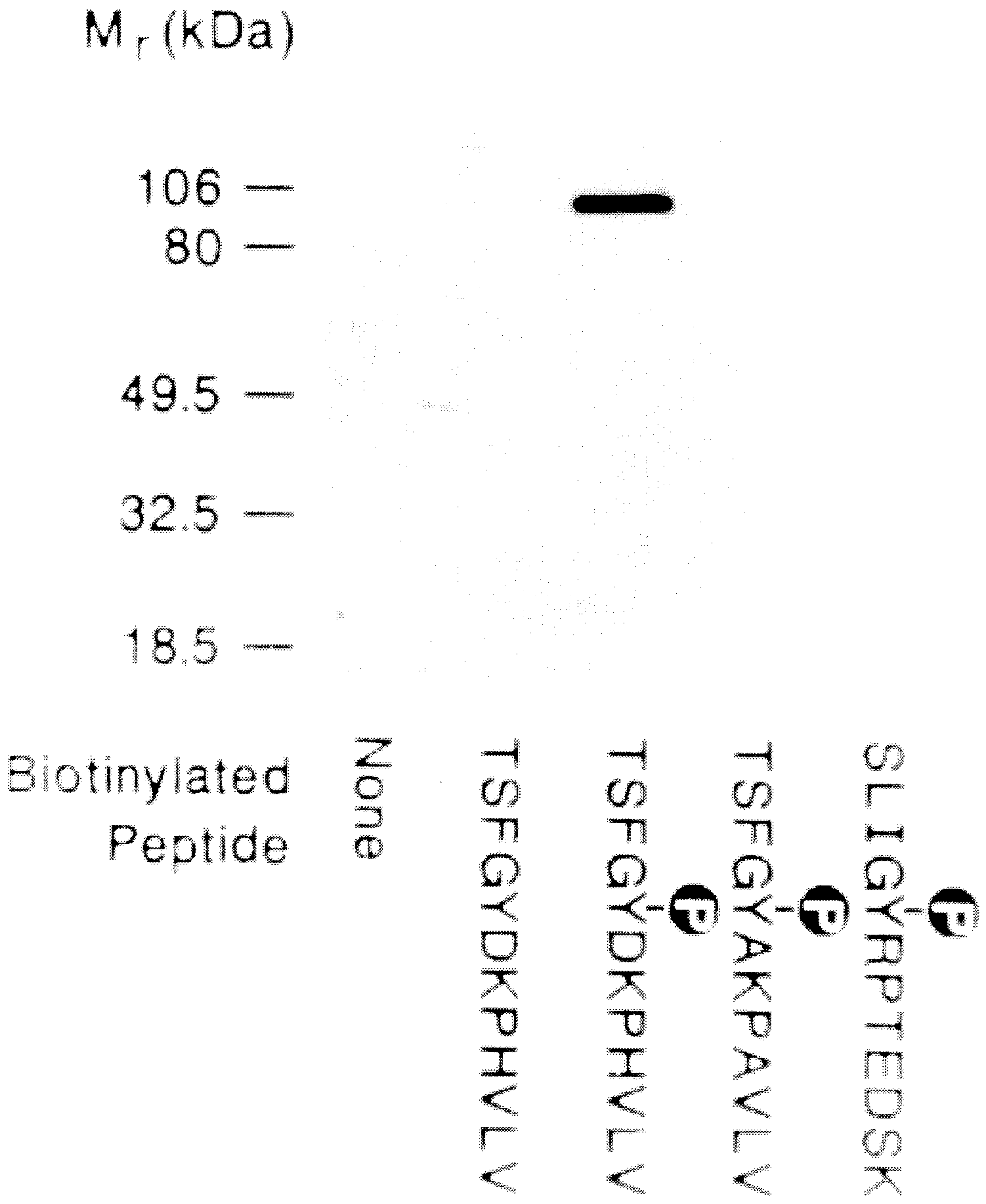
FIG. 6 is a western blot showing the analysis of a representative coprecipition experiment in which p91 was identified to interact specifically with a peptide containing SEQ ID NO:1.
Figure 6B:
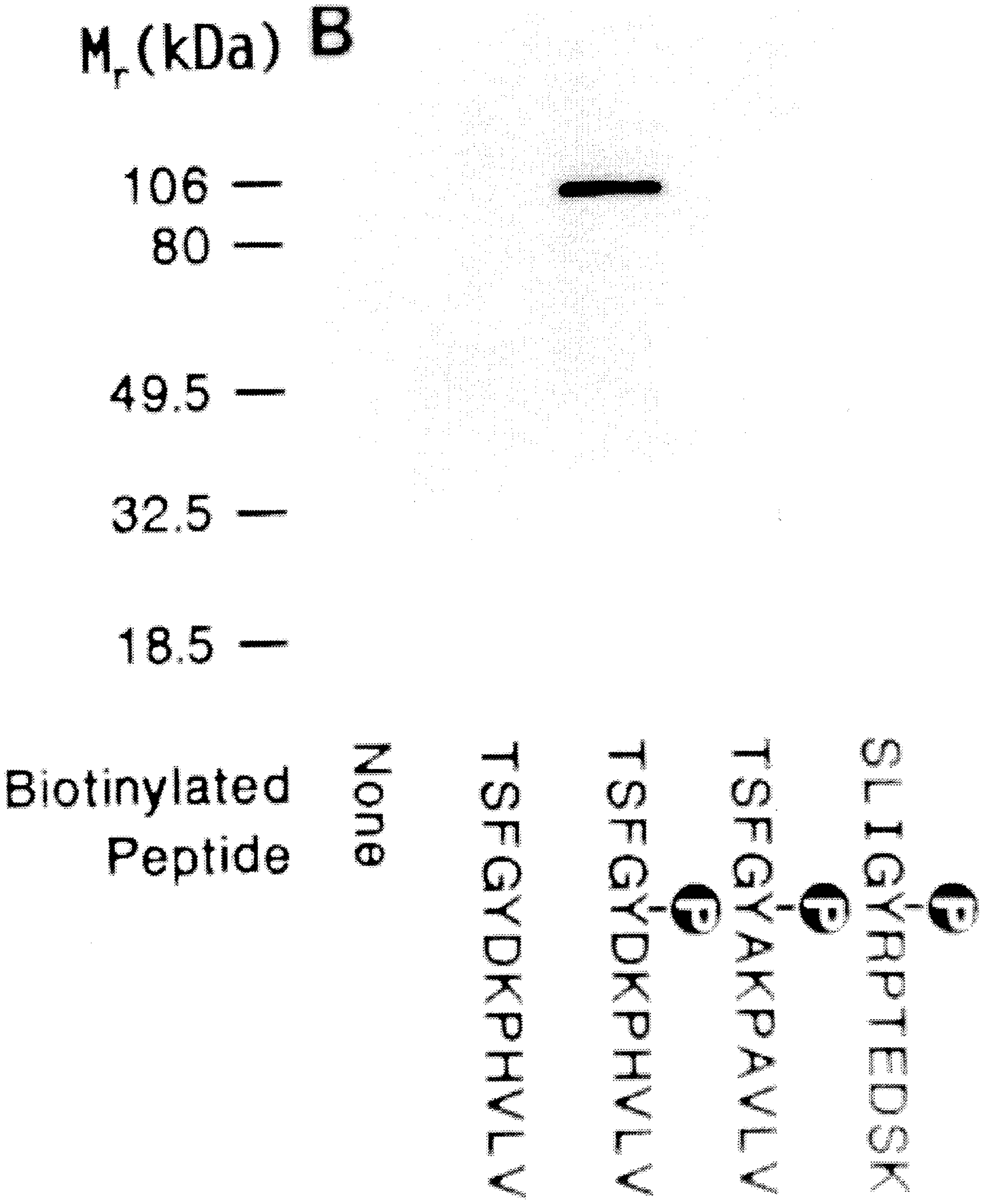

FIG. 6 shows the analysis of a representative coprecipitation experiment in which p91 was identified by western blotting using an antiserum specific for the carboxy terminal portion of the human p91 molecule. Panel A cell homogenates were incubated in the absence of IFNγ, whereas the cell homogenates in Panel B were stimulated with IFNγ. No p91 is precipitated either in the absence of peptide (Lane 1) or in the presence of nonphosphorylated, biotinylated wild type peptide consisting of receptor α chain residues 436–447 (TSFGYDKPHVLV, SEQ ID NO:18, Lane 2). In contrast, p91 is clearly evident in precipitates formed with phosphorylated, biotinylated 436–447 peptide (TSFGY-PO4DKPHVLV, SEQ ID NO:4, Lane 3). The specificity of the interaction between p91 and receptor derived phosphopeptide observed using this direct binding approach corresponds perfectly with that observed using the EMSA functional assay. No interaction of p91 can be detected either with a phosphorylated, biotinylated mutant 436–447 peptide that contains alanine substitutions for the two functionally critical D441 and H444 amino acids (SEQ ID NO:19, Lane 4) or with a phosphorylated, biotinylated peptide derived from a receptor α chain sequence (458–469) that encompasses a functionally unimportant tyrosine residue (Y462, SEQ ID NO:17, Lane 5). Thus, a peptide containing a phosphorylated tyrosine in a sequence corresponding to SEQ ID NO:1 is capable of specifically binding the transcription factor p91 and inhibit its DNA binding activity. It is likely that this phosphotyrosine containing receptor derived sequence, or a derivative or functional equivalent, is useful in inhibiting the development of IFNγ induced biological responses in intact cells.

REFERENCES

Aguet, M., Dembic, Z. and Merlin, G. (1988) *Cell*, 55, 273–280.

Caprino, L. A. and Han, G. Y. (1972) *J. Org. Chem.*, 37, 3404.

Celada, A., Allen, R., Esparza, I., Gray, P. W. and Schreiber, R. D. (1985) *J. Clin. Invest.*, 76, 2196–2205.

David, M. and Larner, A. C. (1992) *Science*, 257, 813–815.

Decker, D., Lew, D. J., Mirkovitch, J. and Darnell, J. E. (1991) *EMBO Journal*, 10, 927–932.

Farrar, M. A., Fernandez-Luna, J. and Schreiber, R. D. (1991) *J. Biol. Chem.*, 266, 19626–19635.

Farrar, M. A., Campbell, J. D. and Schreiber, R. D. (1992) *Proc. Natl. Acad. Sci. USA*, 89, 11706–11710.

Fischer, T., Rehm, A., Aguet, M. and Pfizenmaier, K. (1990) *Cytokine,* 2, 157–161.

Fu, X-Y., Schindler, C., Improta, T., Aebersold, R. and Darnell, J. E., Jr. (1993) *Proc. Natl. Acad. Sci. USA,* 89, 7840–7843.

Gibbs, V. C., Williams, S. R., Gray, P. W., Schreiber, R. D., Pennica, D., Rice, G. and Goeddel, D. V. (1991) *Mol. Cell. Biol.,* 11, 5860–5866.

Hemmi, S., Merlin, G. and Aguet, M. (1992) *Proc. Natl. Acad. Sci. USA,* 89, 2737–2741.

Hershey, G. K. and Schreiber, R. D. (1989) *J. Biol. Chem.,* 264, 11981–11988.

Hershey, G. K., McCourt, D. W. and Schreiber, R. D. (1990) *J. Biol. Chem.,* 265, 17868–17875.

Igarashi, K., David, M., Finbloom, D. S. and Larner, A. C. (1993) *Molec. Cell. Biol.,* 13, 1634–1640.

Janssen, J. W. G., Collard, J. G., Tulp, A., Cox, D., Millington-Ward, A. and Pearson, P. (1986) *Cyto,* 7, 411–417.

Jung, V., Rashidbaigi, A., Jones, C., Tischfield, J. A., Shows, T. B. and Pestka, S. (1987) *Proc. Natl. Acad. Sci. USA,* 84, 4151–4155.

Jung, V., Jones, C., Kumar, C. S., Stefanos, S., O'Connell, S. and Pestka, S. (1990) *J. Biol. Chem.,* 265, 1827–1830.

Kitas, E. A., Knorr, R., Trzeciak, A. and Bannwarth, W. (1991) *Helv. Chim. Acta,* 74, 1314–1329.

Pearse, R. N., Feinman, R., Shuai, K., Darnell, J. E., Jr. and Ravetch, J. V. (1993) *Proc. Natl. Acad. Sci. USA,* 90, 4314–4318.

Raziuddin, A., Sarkar, F. H., Dutkowski, R., Shulman, L., Ruddle, F. H. and Gupta, S. L. (1984) *Proc. Natl. Acad. Sci. U.S.A.,* 81, 5504–5508.

Schindler, C., Fu, X. , Improta, T., Aebersold, R. and Darnell, J. E. Jr. (1992) *Proc. Natl. Acad. Sci. USA,* 89, 7836–7839.

Shuai, K., Schindler, C., Prezioso, V. R. and Darnell, J. E. Jr. (1993) *Science,* 258, 1808–1812.

What is claimed is:

1. A composition of matter comprising an isolated peptide containing the sequence of SEQ ID NO:1 ($Xaa_1$-Asp-$Xaa_2$-$Xaa_3$-His, where $Xaa_1$ is a phosphorylated tyrosine, and $Xaa_2$ and $Xaa_3$ are any amino acid), or a derivative thereof, that specifically binds to transcription factor p91 in a manner inhibiting its transcriptional initiating properties elicited by interferonγ.

2. The composition of claim 1 wherein said peptide has the sequence of SEQ ID NO:3 (Thr-Ser-Phe-Gly-$Xaa_1$-Asp-Lys-Pro-His) or SEQ ID NO:4 (Thr-Ser-Phe-Gly-$Xaa_1$-Asp-Lys-Pro-His-Val-Leu-Val) where $Xaa_1$ is phosphorylated tyrosine.

* * * * *